United States Patent [19]
Suzuki et al.

[11] Patent Number: 5,830,124
[45] Date of Patent: Nov. 3, 1998

[54] GUIDE STRUCTURE FOR ELECTRONIC ENDOSCOPE SYSTEMS

[75] Inventors: Shigeo Suzuki; Fujio Okada, both of Omiya, Japan

[73] Assignee: Fuji Photo Optical Co., Ltd., Omiya, Japan

[21] Appl. No.: 634,881

[22] Filed: Apr. 19, 1996

[30] Foreign Application Priority Data

May 18, 1995 [JP] Japan .................................... 7-143959
May 18, 1995 [JP] Japan .................................... 7-143960

[51] Int. Cl.⁶ ...................................................... A61B 1/04
[52] U.S. Cl. ........................... 600/134; 600/132; 439/628
[58] Field of Search .................................. 600/109, 132, 600/134; 439/620, 628, 944

[56] References Cited

U.S. PATENT DOCUMENTS

| | | | |
|---|---|---|---|
| 4,708,126 | 11/1987 | Toda | 600/132 |
| 4,814,648 | 3/1989 | Hynecek | 327/563 |
| 4,934,960 | 6/1990 | Capp | 439/620 |
| 5,221,216 | 6/1993 | Gabany | 439/620 |
| 5,390,662 | 2/1995 | Okada | 600/134 |
| 5,402,769 | 4/1995 | Tsuji | 600/109 |
| 5,580,280 | 12/1996 | Minich | 439/620 |

*Primary Examiner*—Jeffrey A. Smith
*Assistant Examiner*—Ira Hatton
*Attorney, Agent, or Firm*—Ronald R. Snider

[57] ABSTRACT

A connector guide structure for electronic endoscope systems capable of efficiently eliminating high-frequency noises which are allowed by a connector guide functioning as an antenna to mix by way of sheath members and a console. The connector guide structure comprises a connector guide for connecting a connector disposed on an electronic endoscope to a main unit, and noise eliminating capacitors are connected between the connector guide and a console of the main unit. A capacitor for eliminating noises produced by a radio knife and a plurality of capacitors for eliminating noises produced by clock-frequency signals are used as the capacitors. Feet of the capacitors are directly connected within an interval of 4 mm to 20 mm which is reserved between the connector guide and the console. Accordingly, the connector guide structure is capable of favorably eliminating not only the noises produced by the radio knife but also the noises produced by providing clock-frequency signals.

5 Claims, 7 Drawing Sheets

GUIDE STRUCTURE FOR ELECTRONIC ENDOSCOPE SYSTEMS

BACKGROUND OF THE INVENTION

This application claims the priority of Japanese Patent Application Nos. 7-143959 and 7-143960, filed on May 18th, 1995 which are incorporated herein by reference.

1. Field of the Invention

The present invention relates to a connector guide which is to be used for connecting a connector disposed on an electronic endoscope to a main unit of an electronic endoscope system and more specifically a structure thereof for eliminating noises.

2. Description of the Prior Art

FIG. 13 schematically shows a configuration of an electronic endoscope system, wherein an electronic endoscope 1 is connected to a main unit 2 comprising a signal processing circuit (referred to also as a processor unit). The electronic endoscope 1 has a CCD (charge coupled device), or a solid-state device, disposed on a distal end 3 thereof as well as a rotating knob 5 and a forceps port 6 disposed on a control section 4 thereof. The forceps port 6 is communicated with an internal treating tool passage channel so that a treating tool can be inserted through the forceps port 6 to the distal end 3. The electronic endoscope 1 which is configured as described above is connected to the main unit 2 by way of a cable 9 which has a connector 7 for a light guide and another connector 8 for a signal line. In addition, the main unit 2 is connected to an observation monitor (not shown).

In the electronic endoscope system described above, rays emitted from a light source are led to the electronic endoscope 1 through the light guide connector 7 and the cable 9, thereafter being supplied from the distal end 3 to an interior of a body to be observed. An image of the body is captured by the CCD, which provides video signals to the main unit 2 through the cable 9 and the signal line connector 8. The video signals are subjected to predetermined processings and sent to the monitor for allowing the image of the body to be observed on the monitor.

On the other hand, the electronic endoscope system allows a variety of treat performed, while observing the image on the monitor, with treating tools inserted into the interior of the body to be observed from the distal end 3. The electronic endoscope system is usable, for example, to cut off an affected part by using a radio knife.

The electronic endoscope system described above poses a problem that it allows high-frequency noises produced, for example during an operation with the radio knife, to mix with the video signals, thereby hindering formation of a favorable image. For this reason, the electronic endoscope 1 conventionally adopted a structure wherein shielding members were disposed on outer circumferences of the treating tool passage channel, the signal line, etc. or circuits disposed in the main unit 2 so that noise components captured by the shielding members were grounded in a signal system.

However, a further improvement is required since the noise components produced by the radio knife, for example, cannot be completely eliminated simply by disposing the shielding members. The applicant paid attention to and attempted to eliminate noise components induced during the operation of the radio knife and noise components radiated by higher harmonics of a CCD driving clock out of the high-frequency noises mixing by way of sheath members and connector guide on the electronic endoscope 1.

Speaking more concretely with reference to FIG. 13, disposed on the main unit 2 are connector guides (scope guides) 10 and 11 for guiding and holding connectors 7 and 8 which are connected thereto. Since the connector guides 10 and 11 (the latter in particular) are electrically floated from the console 2, they function as antennae and receive the high-frequency noises from the radio knife or the like.

Further, an oscillator circuit disposed in the main unit 2 provides clock-frequency signals (for example of 14.3 MHz) to the electronic endoscope 1 for CCD driving pulses, etc. and it has been confirmed that noises produced by the clock-frequency signals are radiated from the connector guide 11 functioning as the antenna, thereby producing high-frequency noises having frequencies different from those of the noises produced by the radio knife. Therefore, it is also necessary to eliminate the noises produced by the clock-frequency signals.

BRIEF SUMMARY OF THE INVENTION

In view of the problems described above, it is a primary object of the present invention to provide a connector guide structure for electronic endoscope systems which is capable of favorably eliminating not only the high-frequency noises produced by a radio knife out of those mixing through sheath members and a console but also the noises produced by providing the clock-frequency signals.

For accomplishing this object, the connector guide structure for electronic endoscope systems according to the present invention is characterized in that it is configured to comprise a main unit of an electronic endoscope system, a connector disposed on an electronic endoscope, a connector guide which is disposed for connecting the connector on the electronic endoscope to the main unit and electrically insulated from a console of the main unit, and a noise eliminating capacitor (fixed capacitor) between the connector guide and the main unit console.

Speaking of the high-frequency noises produced by the radio knife, for example, components which have frequencies integral times (x1, x2, x3, . . . ) as high as 150 kHz and not exceeding 2 MHz appear on a monitor and deteriorate image qualities. It is therefore possible to favorably eliminate the high-frequency noises produced from the radio knife by using a high-frequency capacitor which eliminate the components described above.

Another invention makes it possible to eliminate high-frequency (higher harmonic) noises produced by the clock-frequency signals by using, as the capacitor mentioned above, a capacitor which has resonance points (minimum impedance) at frequencies integral times as high as a clock frequency, for example, of 14.3 MHz for driving the CCD of the electronic endoscope. In addition, it is possible to use the above-mentioned capacitor for eliminating the noises produced by the radio knife in combination with the capacitor for eliminating the noises produced by the clock-frequency signals.

It is preferable that the noise eliminating capacitor is disposed between the connector guide and the main unit console without using separate lead wires but by directly connecting feet which are formed integrally therewith and that the feet are preliminarily cut as short as possible. When the feet are cut as short as possible, the capacitor has impedance lowered due to removed inductance components of the cut-off portions of the feet, thereby eliminating the high-frequency noises, those having higher frequencies at higher efficiencies in particular.

Further, It is possible to select, as the noise eliminating capacitor, a capacitor of a type which has a body connectable with screws and dispose this capacitor directly between the connector guide and the main unit console.

Furthermore, it is desirable for disposing the noise eliminating capacitor to reserve a space within a range from 4 mm to 20 mm between the connector guide and the main unit console.

Moreover, according to still another invention which uses the above-mentioned capacitor for eliminating the noises produced by the clock-frequency signals, it is possible to use a plurality of capacitors which have high-frequency characteristics different from one another. The high-frequency (higher harmonic) noises produced by the clock-frequency signals can be eliminated favorably by using a plurality of capacitors having resonance points at frequencies integral times (x1, x2, x3, . . . ) as high as a clock frequency, for example, 14.3 MHz, used in the electronic endoscope and different from one another.

DETAILED DESCRIPTION OF THE PREFERRED EMBODIMENTS

Figure 1:
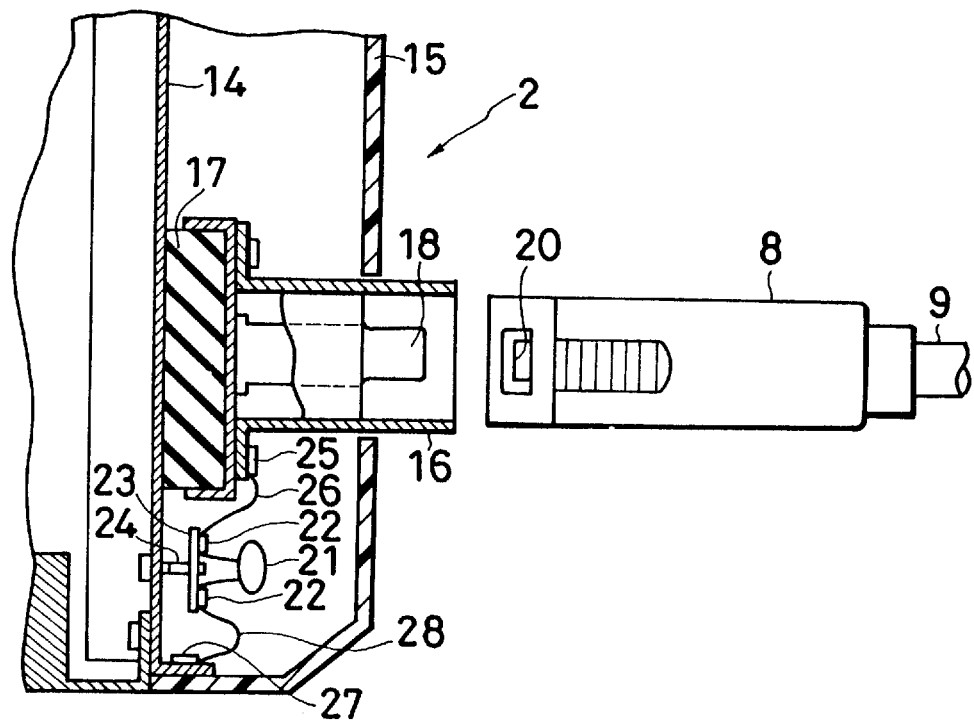
FIG. 1 is a sectional view taken along I—I line in FIG. 2 illustrating a configuration of a first embodiment of the connector guide structure for electronic endoscope systems according to the present invention.
Figure 2:
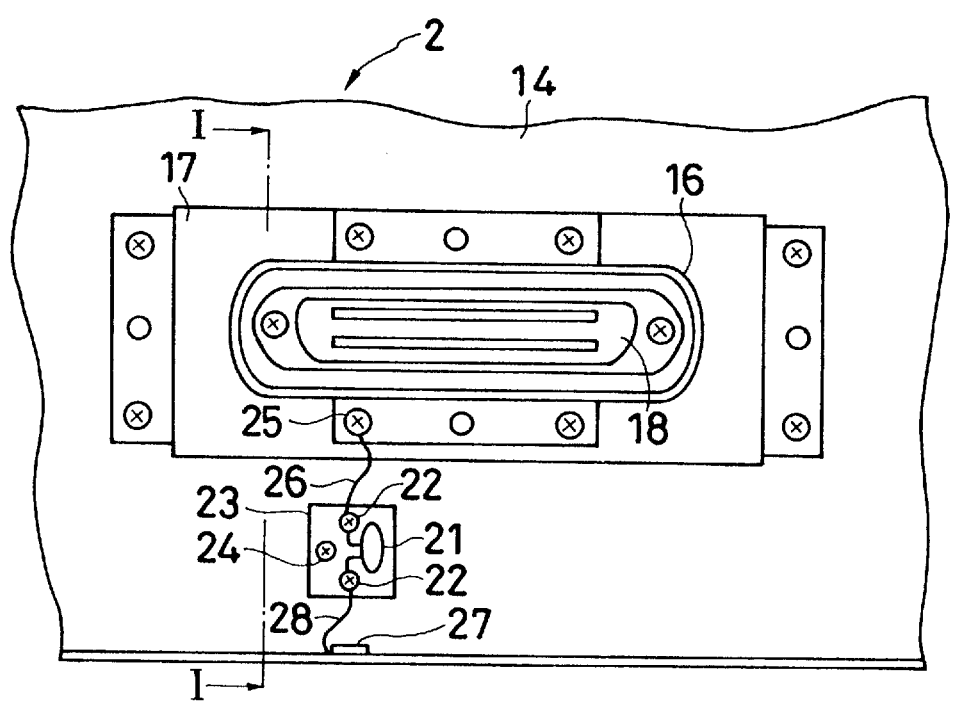
FIG. 2 is a front view of a connector guide shown in FIG. 1.

Shown in FIGS. 1 and 2 is a configuration of a first embodiment of the connector guide (scope guide) structure for electronic endoscope systems according to the present invention which is configured for a signal line connector. A main unit 2 comprising a signal processor circuit shown in these drawings is similar to that shown in FIG. 13. In front of the main unit 2, a metallic console 14 is covered with a panel 15 made of a resin material. A metallic connector guide 16 is disposed in an aperture formed in the panel 15 and connected to the console 14 by way of a bakelite plate 17 which is an insulating material. A connector member 18 which has a plurality of terminals is to be set in the connector guide 16.

On the side of an electronic endoscope, on the other hand, a connector (for the signal line) 8 is attached to an end of a cable 9 and disposed in the connector 8 is a connector member which has a plurality of terminals and is configured to fit over the connector member 18. Disposed on a side of the connector 8 is a claw member 20 which is configured to engage with a groove formed in an inside surface of the connector guide 16.

In the configuration described above, a capacitor 21 for eliminating high-frequency noises is fixed with screws 22 to a fixing member 23, which in turn is attached to the console 14 with a screw 24. Further, one of the screws 22 on the fixing member 23 is connected to a setscrew 25 on the connector guide 16 through a lead wire 26, whereas the other screw 22 is connected to a setscrew 27 on the console 14 through a lead wire 28.

Used as the capacitor 21 in the first embodiment is a ceramic capacitor or the like, for example, which is capable of favorably eliminating the high-frequency noises produced, for example, by a radio knife. Since the noises produced by the radio knife have frequencies around 150 kHz, the first embodiment adopts a capacitor which has low impedance for signals at frequencies up to approximately 20 times as high as 150 kHz. This capacitor is also capable of eliminating, to certain degrees, the high-frequency noises produced by the clock-frequency signals of 14.3 MHz to be used for the CCD driving circuit and other circuits. Reversely, it is possible to eliminate the high-frequency noises produced by the clock-frequency signals in particular by selecting, as the capacitor 21, a capacitor which has resonance points at frequencies integral times (x1, x2, x3, . . . ) as high as the clock frequency.

Figure 3:
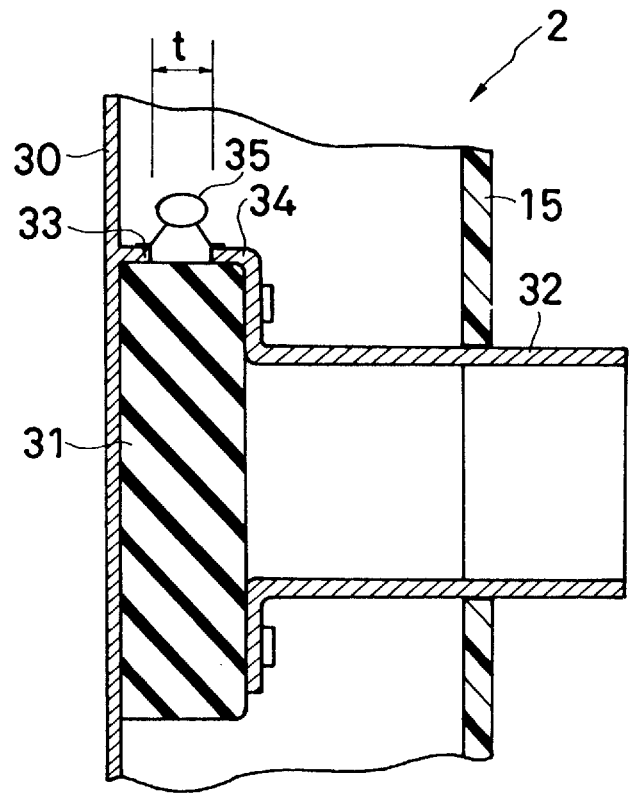
FIG. 3 is a side sectional view illustrating a configuration of a second embodiment of the connector guide structure according to the present invention.
Figure 4:
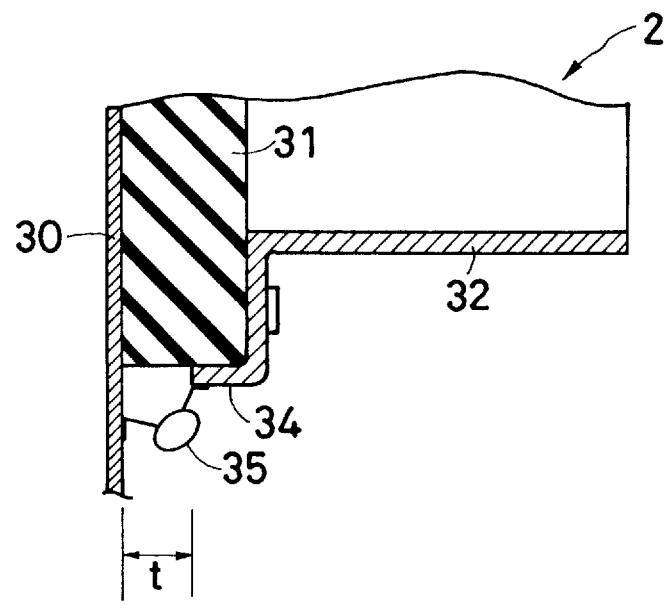
FIG. 4 is a side sectional view illustrating a different connecting structure for a capacitor in the second embodiment.

Shown in FIGS. 3 and 4 is a configuration of a second embodiment of the connector guide structure according to the present invention which is configured to eliminate the high-frequency noises at higher efficiencies. Attached to a console 30 of a main unit 2 is a connector guide 32, as shown in FIG. 3, by way of a bakelite plate 31 which is an insulating material. Formed on the console 30 and the connector guide 32 are a protrusion 33 and an extension 34 respectively at an interval t of approximately 4 to 20 mm, or more preferably 6 to 10 mm.

A capacitor 35 having low impedance at frequencies up to approximately 20 times as high as 150 kHz, for example, is directly connected by soldering or the like between the protrusion 33 and the extension 34. In the second embodiment, feet formed integrally with the capacitor 35 have been preliminarily cut as short as possible. One of the feet of the capacitor 35 may be connected directly to the console 30 without forming the protrusion 33 thereon as shown in FIG. 4.

For directly connecting the capacitor 35 as described above, the interval t should be approximately 4 to 20 mm, or more preferably 6 to 10 mm, for a reason described below. It is desirable to maintain predetermined dielectric strength, for example, of 4 kV between a circuit disposed on a side of a patient (primary circuit) and another circuit disposed on an output side(secondary circuit) in an electronic endoscope system. For the second embodiment wherein the capacitor 35 is disposed along the bakelite plate 31, an interval of approximately 6 mm is required for maintaining dielectric strength of 4 kV. (An interval of approximately 4 mm is sufficient in a case where the capacitor 35 is disposed not along the bakelite plate 31 but in the air.)

For favorably eliminating the high-frequency noises by a circuit which comprises the capacitor 35, it is necessary to lower impedance of the circuit. In the configuration of the first embodiment which comprises the lead wires 26 and 28 in addition to the long feet of the capacitor 21, impedance is enhanced by $2\pi fL$ (f: frequency, L: inductance) due to inductance components of the wires and feet, thereby lowering efficiencies for eliminating the high-frequency noises. It is therefore required to omit the wires and feet as far as possible and inductance is extremely lowered by setting the interval within 20 mm, or more preferably 10 mm.

Comparing with the first embodiment, the second embodiment, which has the configuration wherein the capacitor 35 having the feet cut as short as possible is connected directly between the console 30 and the connector guide 32 (the extension 34), requires neither the lead wire 26 nor wire 27, and has lower inductance, thereby lowering impedance. As a result, capacitor 35 is capable of favorably eliminating the high-frequency noises, those having higher frequencies at higher efficiencies in particular. As a result, the second embodiment is capable of eliminating not only the high-frequency noises produced by a radio knife (having frequencies on the order of 150 kHz) but also the higher harmonic noises produced by providing the clock-frequency signals (having frequencies integral times as high as the clock frequency of 14.3 MHz).

Figure 5:
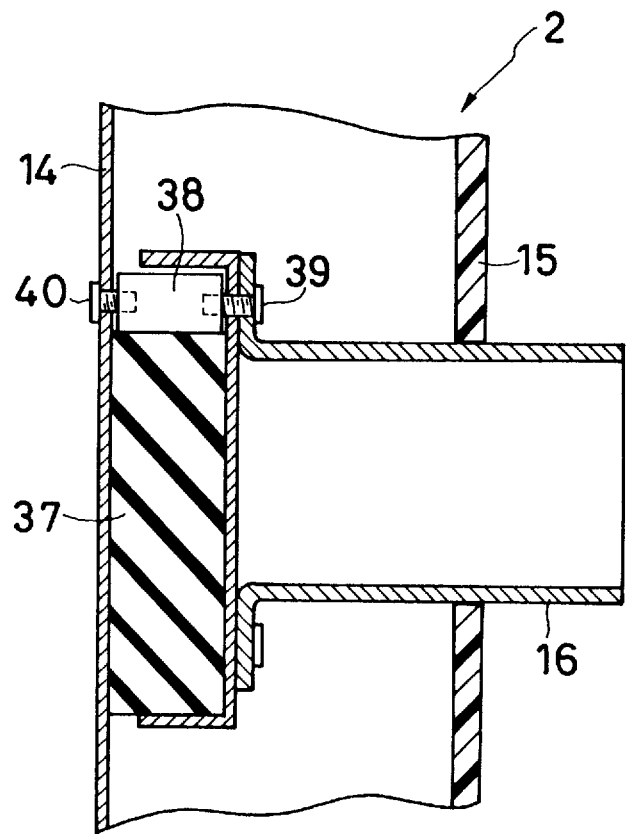
FIG. 5 is a side sectional view illustrating a configuration of a third embodiment of the connector guide structure according to the present invention.
Figure 6:
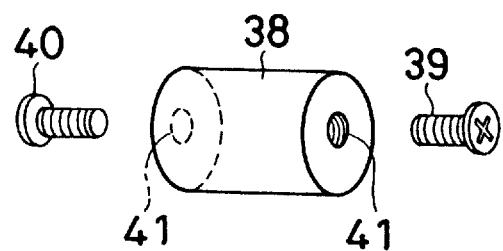
FIG. 6 is a perspective view illustrating a structure of a capacitor shown in FIG. 5.

Illustrated in FIGS. 5 and 6 is a configuration of a third embodiment of the connector guide structure for electronic endoscope systems according to the present invention wherein a screw-connection type or a screw-fixed type capacitor is used. A main unit 2 which is illustrated in FIG. 5 has, like that shown in FIG. 1, a connector guide 16 attached to a console 14 by way of a bakelite plate 37. A cylindrical capacitor 38 is disposed in a space formed, for example, by cutting off an upper end of the bakelite plate 37, and fixed directly with a screw 39 inserted from a side of the connector guide 16 and another screw 40 inserted from a side of the console 14.

The capacitor 38 is tapped as shown in FIG. 6 so as to have, at both ends thereof, screw receivers 41 which function as connecting terminals. The capacitor 38 can be disposed directly between the console 14 and the connector guide 16 since electrical connection of the capacitor 38 can be made by connecting it to the connector guide 16 and the console 14 with the screws 39 and 40 as described above. Neither, the third embodiment requires the lead wire 26 or 28 which was used in the first embodiment and has impedance lowered by removing inductance components of the lead wires 26 and 28. As a result, the third embodiment eliminates not only the high-frequency noises produced by a radio knife but also the higher harmonic noises produced by the clock-frequency signals.

Though the second embodiment and the third embodiment described above are configured to use the capacitors 35 and 38 respectively for eliminating the high-frequency noises produced by the radio knives, these embodiments may be modified to use capacitors which have resonance points at frequencies integral times as high as the clock frequency of 14.3 MHz for eliminating mainly the higher harmonic noises produced by the clock-frequency signals.

Figure 7:
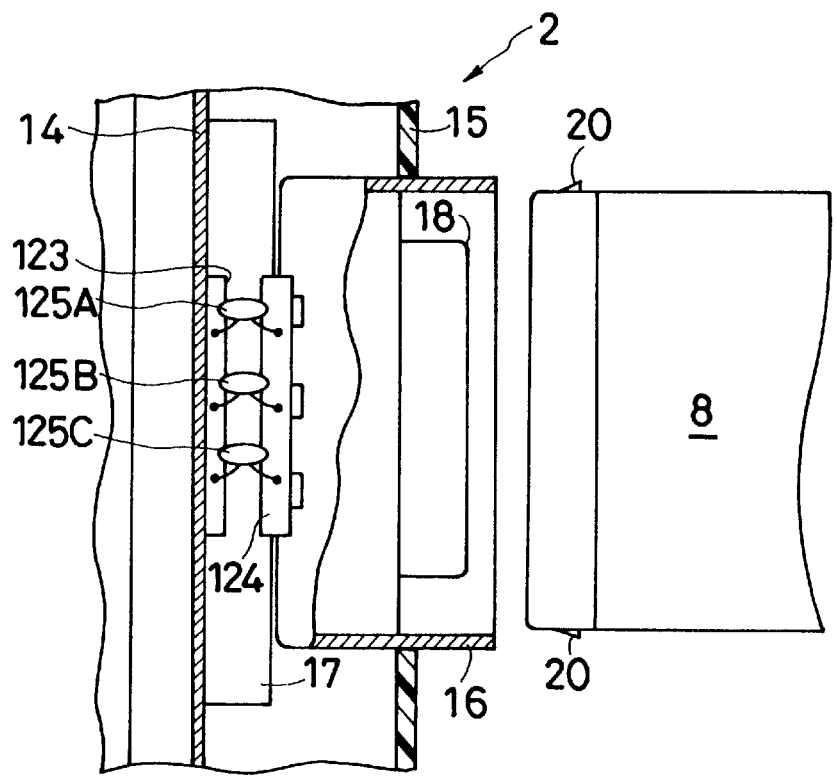
FIG. 7 is a top view illustrating a configuration of a fourth embodiment of the connector guide structure for electronic endoscope system according to the present invention.
Figure 8:
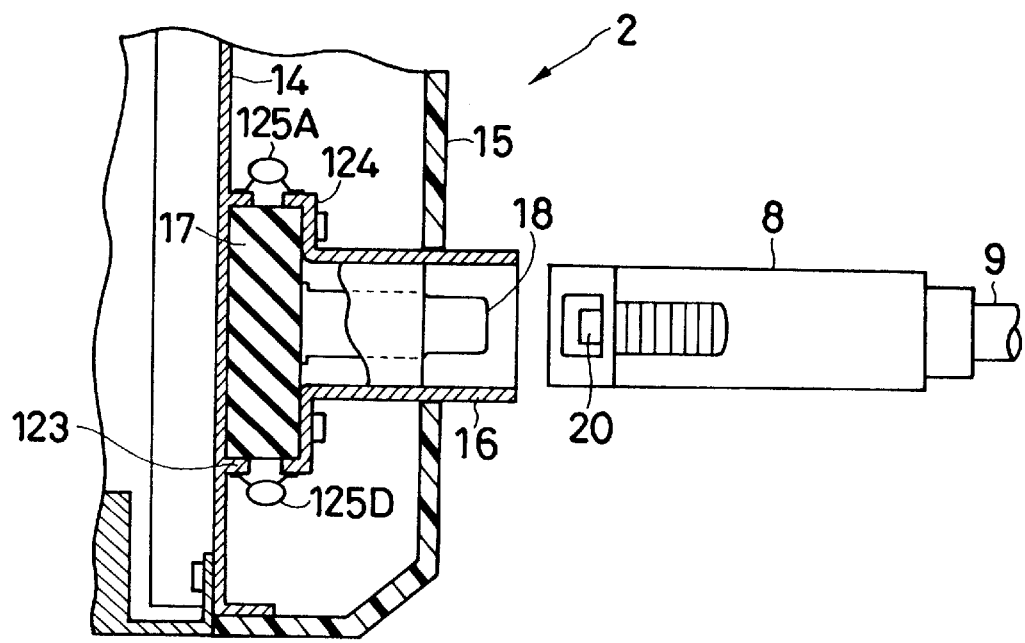
FIG. 8 is a sectional view taken along II—II line in FIG. 9 illustrating a side of a connector guide shown in FIG. 7.
Figure 9:
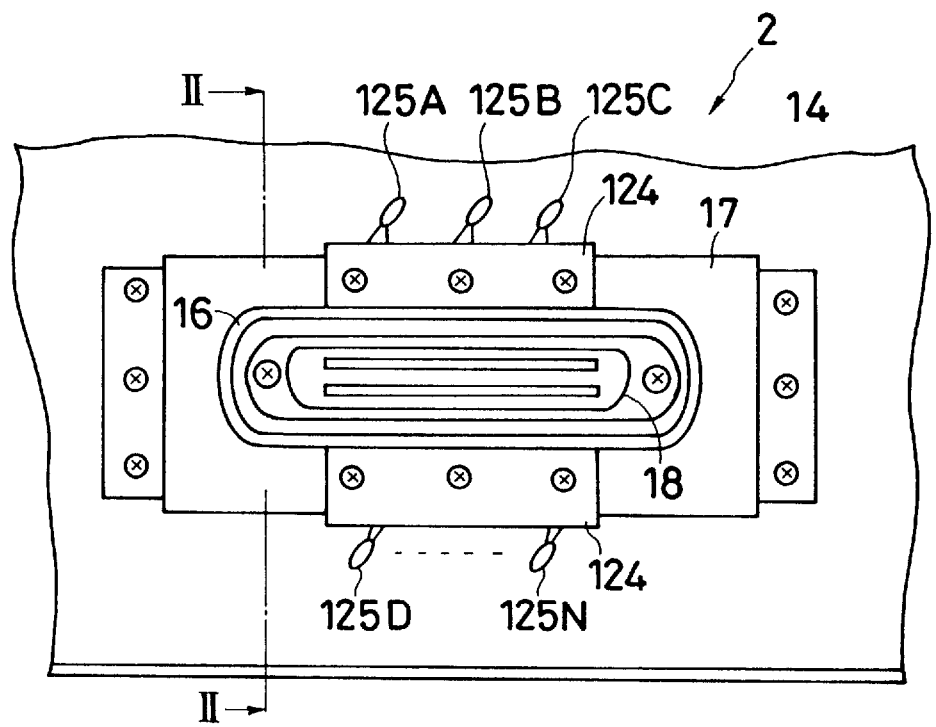
FIG. 9 is a front view illustrating a connector guide shown in FIG. 7.

FIGS. 7 through 9 show a configuration of a fourth embodiment of the connector guide structure according to the present invention wherein a main unit 2 comprising a signal processor circuit is similar to that used in the first embodiment. Disposed in front of a console 14 of a main unit 2 is a metallic connector guide 16 by way of a bakelite plate 17 which is an insulating material and a connector member 18 having a plurality of terminals is disposed in the connector guide 16.

Disposed on a side of an electronic endoscope, on the other hand, is a connector 8 which is configured to fit over the connector member 18 and has, on a side surface thereof, a claw member 20 shaped to engage with a groove formed in an inside surface of the connector guide 16.

In the configuration described above, protrusions 123 are formed integrally with the side surface of the console 14 so as to sandwich the bakelite plate 17 therebetween as shown in FIG. 8 and extensions 124 are formed integrally with ends of the connector guide 16 at locations in opposition to the protrusions 123. In the fourth embodiment also, an interval t of approximately 4 to 20 mm, or more preferably 6 to 10 mm, is reserved between the protrusions 123 and the extensions 124, and a plurality of capacitors 125A, 125B, 125C, 125D, . . . 125N are connected directly between the protrusions 123 and the extensions 124 by soldering or the like. Before connecting the capacitors, their feet are to be cut as short as possible.

Figure 10:
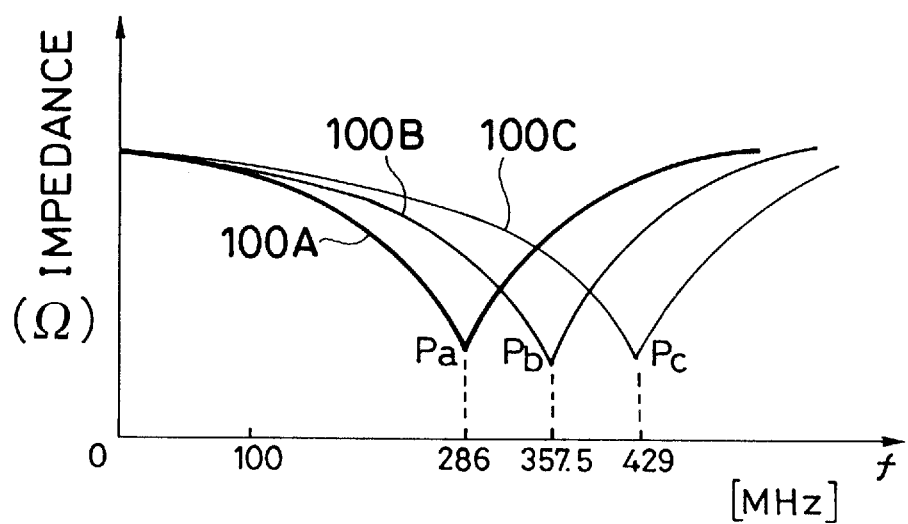
FIG. 10 shows graphs visualizing high-frequency characteristics of a plurality of capacitors used in the fourth embodiment of the present invention.

The plurality of capacitors 125A, 125B, 125C, 125D, . . . 125N have high-frequency characteristics which are different from one another. Exemplified in FIG. 10 are characteristics which are to be selected for eliminating noises produced due to the clock frequency. In this example, capacitor 125A has a capacity of 330 pF and a resonance point Pa at a frequency of 14.3 MHz×20=286 MHz, or a characteristic 100A, capacitor 125B has a capacity of 220 pF and a resonance point Pb at a frequency of 14.3 MHz×25= 357.5 MHz, or a characteristic 100B, and capacitor 125C has a capacity of 100 pF and a resonance point Pc at a frequency of 14.3 MHz×30=429 MHz, or a characteristic 100C. When the connector guide structure uses these three capacitors 125A through 125C, it has an impedance characteristic visualized in FIG. 11, or low impedance within a frequency range from the vicinity of 200 MHz to the vicinity of 500 MHz.

Figure 12:
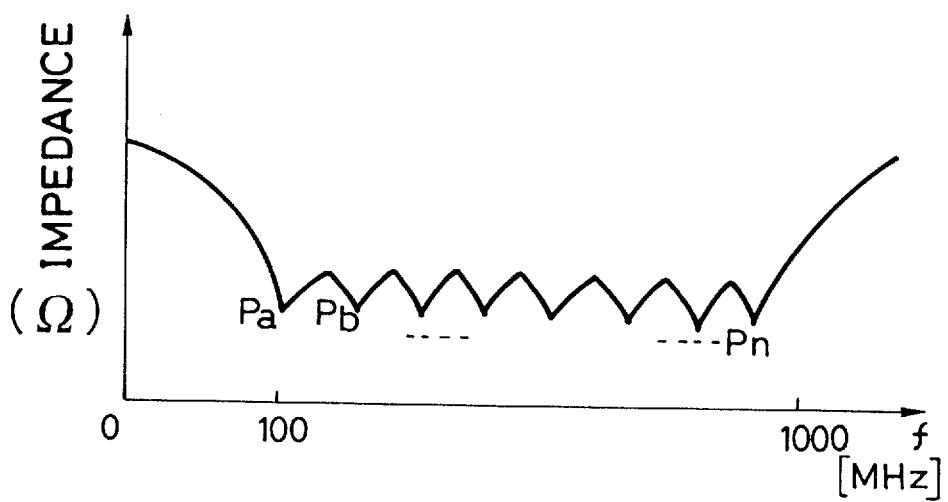
FIG. 12 is a graph illustrating a high-frequency characteristic obtained with the capacitors used in the fourth embodiment of the present invention.

It is also possible to lower impedance within a range from 100 MHz to 1000 MHz as shown in FIG. 12 by adequately selecting high-frequency characteristics (resonance points Pa through Pn) for capacitors 125A through 125N.

For eliminating the high-frequency noises produced by a radio knife, the fourth embodiment uses an additional capacitor 125D which has a capacity of approximately 1000 pF and is capable of eliminating noises having frequencies, for example, down to approximately 2 MHz. Needless to say, the fourth embodiment may use a capacitor for eliminating the noises produced by the clock-frequency signals and another capacitor for eliminating the noises produced by the radio knife.

As in the cases of the other embodiments, the fourth embodiment adopts an interval t of approximately 4 to 20 mm, or more preferably 6 to 10 mm, for disposing the capacitors 125 between the console 14 and the connector guide 16. An interval on the order of 6 mm is required for maintaining dielectric strength, for example, of 4 kV between a circuit disposed on a side of a patient and a circuit disposed on an output side. (An interval of approximately 4 mm is sufficient when the capacitors are disposed not along the bakelite plate 17 but in the air.) When the capacitors 125 are connected through lead wires, the connector guide structure will have impedance enhanced by $2\pi fL$ (f: frequency, L: inductance) due to inductance components of the lead wires, thereby lowering noise eliminating efficiencies. It is therefore possible to lower inductance and enhance noise eliminating efficiencies by connecting the capacitors with no lead wires and reserving an interval within 20 mm, or more preferably within 10 mm, between the console 14 and the connector guide 16.

Figure 11:
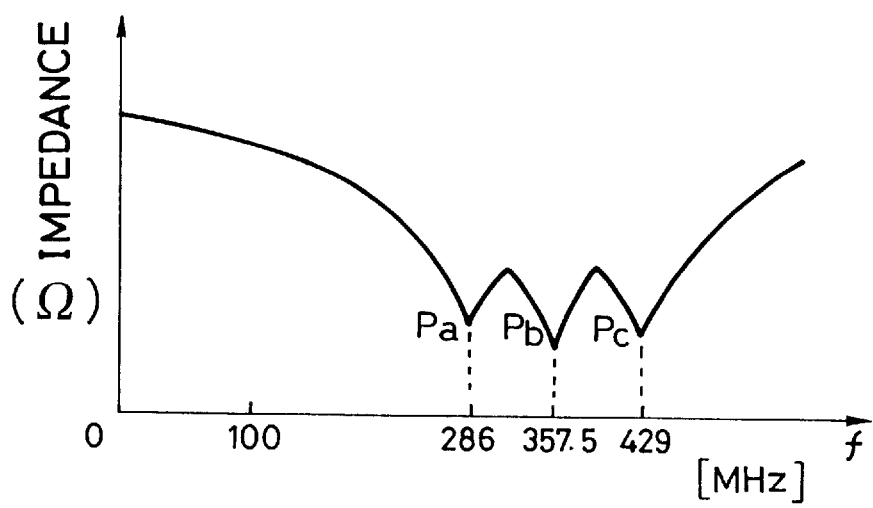
FIG. 11 is a curve illustrating a high-frequency characteristic obtained with the capacitors shown in FIG. 10.

The fourth embodiment, which comprises capacitor 125A, 125B and 125C having resonance points at frequencies integral times as high as the clock frequency of 14.3 MHz as illustrated in FIGS. 11 and 12, is capable of favorably eliminating the high-frequency noises produced by providing the clock frequency signals. Further, the fourth embodiment which uses capacitor 125D is capable of favorably eliminating the high-frequency noises produced by the radio knife.

Since the capacitors having feet which are cut as short as possible are connected directly between the console 14 and the connector guide 16 in the fourth embodiment, it requires no lead wires and has reduced inductance, thereby lowering impedance. As a result, the fourth embodiments capable of eliminating the high-frequency noises at efficiencies.

Though capacitors 125A through 125N are connected separately in the fourth embodiment described above, it may be modified so that a printed circuit board or the like on which a plurality of capacitors have preliminarily been mounted can be connected at a time between the protrusions 23 formed on the console 14 and terminal sections disposed on the extensions 24 of the connector guide 16.

Figure 13:
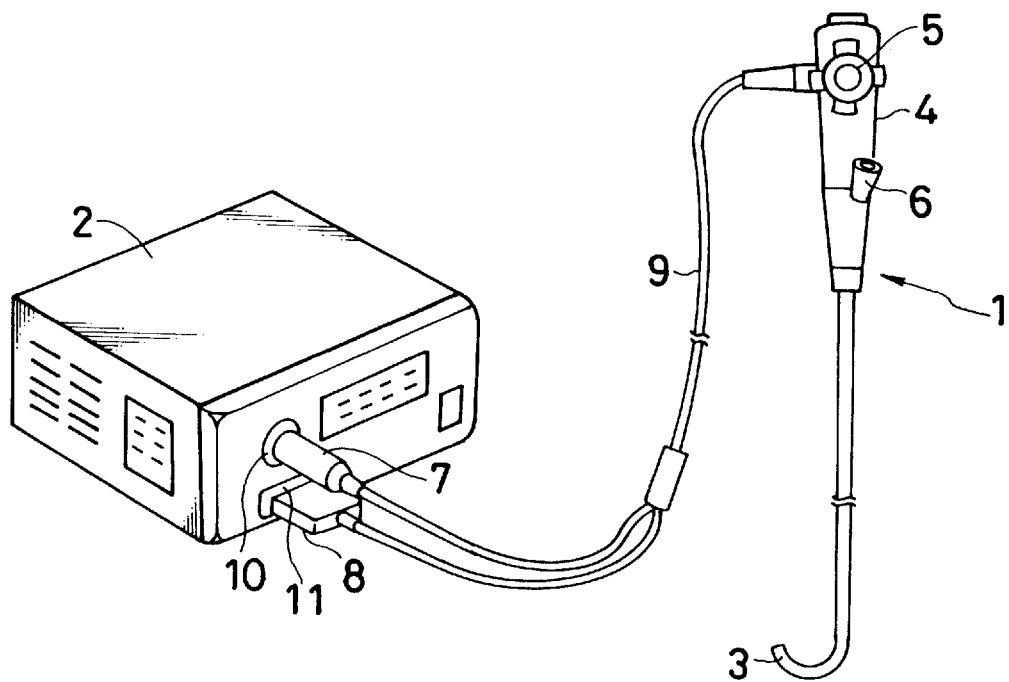
FIG. 13 is a perspective view illustrating an overall configuration of a conventional electronic endoscope system.

Though each of the embodiments described above is configured for eliminating noises in the connector guide 16 for a signal line connector 8 (11 in FIG. 13), the connector guide structure according to the present invention is applicable also to the connector guide for a light guide connector 7 (10 in FIG. 13).

What is claimed is:

1. A connector guide structure for electronic endoscope systems comprising:

a main unit of an electronic endoscope system;

a connector disposed on an electronic endoscope;

a connector guide which is disposed for connecting said connector on the electronic endoscope to said main unit and electrically insulated from a console of the main unit;

a noise eliminating capacitor disposed between said connector guide and said console of the main unit; and wherein an interval within a range from 4 mm to 20 mm is reserved between said connector guide and said console of the main unit for connecting said noise eliminating capacitor.

2. A connector guide structure for electronic endoscope systems comprising:

a main unit of an electronic endoscope system;

a connector disposed on an electronic endoscope;

a connector guide which is disposed for connecting said connector on the electronic endoscope to said main units and electrically insulated from a console of the main unit;

a noise eliminating capacitor disposed between said connector guide and said console of the main unit; and wherein used as said noise eliminating capacitor is a capacitor which has resonance points at frequencies integral times as high as frequencies of noises produced from a radio knife and functions to eliminate the noises produced from the radio knife.

3. A connector guide structure for electronic endoscope systems comprising:

a main unit of an electronic endoscope system;

a connector disposed on an electronic endoscope;

a connector guide which is disposed for connecting said connector on the electronic endoscope to said main unit and electrically insulated from a console of said main unit; and a capacitor which is disposed between said connector guide and said console of the main unit, and has a high-frequency characteristic exhibiting minimum impedance at frequencies integral times as high as a clock frequency for eliminating noises produced by clock-frequency signals.

4. A connector guide structure for electronic endoscope systems according to claim 3 wherein a capacitor for eliminating noises produced by a radio knife is used in combination with said capacitor for eliminating the noises produced by the clock-frequency signals.

5. A connector guide structure for electronic endoscope systems according to claim 3 wherein a plurality of capacitors having high-frequency characteristics different from one another are used for eliminating the noises produced by the clock-frequency signals.

* * * * *